United States Patent
Brendzel et al.

(10) Patent No.: US 7,632,309 B1
(45) Date of Patent: Dec. 15, 2009

(54) PYROLYTIC CARBON AND METAL/METALLOID CARBIDE COMPOSITES

(75) Inventors: Avrom M. Brendzel, Roseville, MN (US); Richard Rodriguez, White Bear Lake, MN (US); Michelle Lund Toy, North St. Paul, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/460,140

(22) Filed: Dec. 13, 1999

(51) Int. Cl.
*A61F 2/24* (2006.01)
(52) U.S. Cl. .................................................. 623/2.42
(58) Field of Classification Search ............... 623/2.41, 623/2.42, 22.42; 501/86, 87, 90
See application file for complete search history.

(56) References Cited

U.S. PATENT DOCUMENTS

| | | | |
|---|---|---|---|
| 3,579,645 A | 5/1971 | Bokros | 3/1 |
| 3,677,795 A | 7/1972 | Bokros et al. | 117/46 |
| 3,685,059 A | 8/1972 | Bokros et al. | 3/1 |
| 3,738,906 A * | 6/1973 | Olcott | 161/168 |
| 3,783,868 A * | 1/1974 | Bokros et al. | 128/260 |
| 3,877,080 A * | 4/1975 | Olcott | 623/23.51 |
| 3,969,130 A * | 7/1976 | Bokros | 117/332 |
| 4,822,355 A | 4/1989 | Bhuvaneshwar | 623/2 |
| 5,080,668 A | 1/1992 | Bolz et al. | 623/2 |
| 5,498,442 A | 3/1996 | Lennartz | 427/6 |
| 5,605,714 A | 2/1997 | Dearnaley et al. | 427/2.24 |
| 5,607,469 A | 3/1997 | Frey | 623/2 |
| 5,725,573 A | 3/1998 | Dearnaley et al. | 623/2 |
| 5,782,910 A * | 7/1998 | Davidson | 623/3 |
| 6,258,737 B1 * | 7/2001 | Steibel et al. | 442/172 |

FOREIGN PATENT DOCUMENTS

EP 0 159 410 12/1984

OTHER PUBLICATIONS

"Liquid Fluid Bed Coating Process" by, W.J. Lackey, Carbon, International Journal, vol. 34, No. 10, ISSN 0008-6233, 1996.
Cyclic fatigue-crack propagation, stress-corrosion, and fracture-toughness behavior in pyrolytic carbon-coated graphite for prosthetic heart valve applications. J. of Biomedical Materials Research, vol. 24, 189-206 (1990).

* cited by examiner

*Primary Examiner*—Alvin J Stewart
(74) *Attorney, Agent, or Firm*—Hallie A. Finucane; Westman, Champlin & Kelly, P.A.

(57) ABSTRACT

Medical devices can be formed from improved composite materials that include a composition that has at least about 50 percent by volume pyrolytic carbon and a second composition having at least about 50 percent by volume metal/metalloid carbide. The composite material can optionally include a substrate. Some embodiments of the composite material have the pyrolytic carbon material at exposed surfaces.

2 Claims, 7 Drawing Sheets

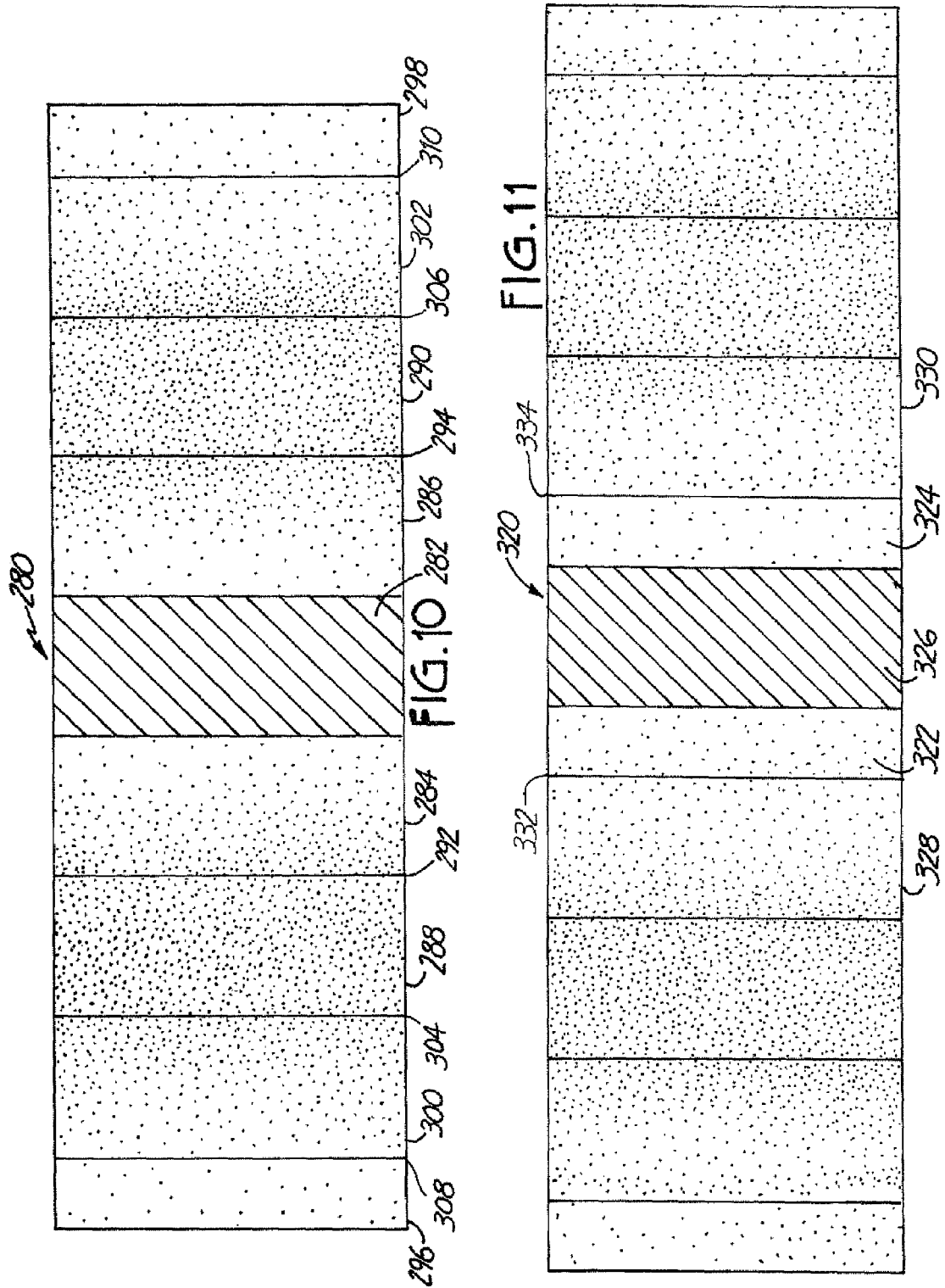

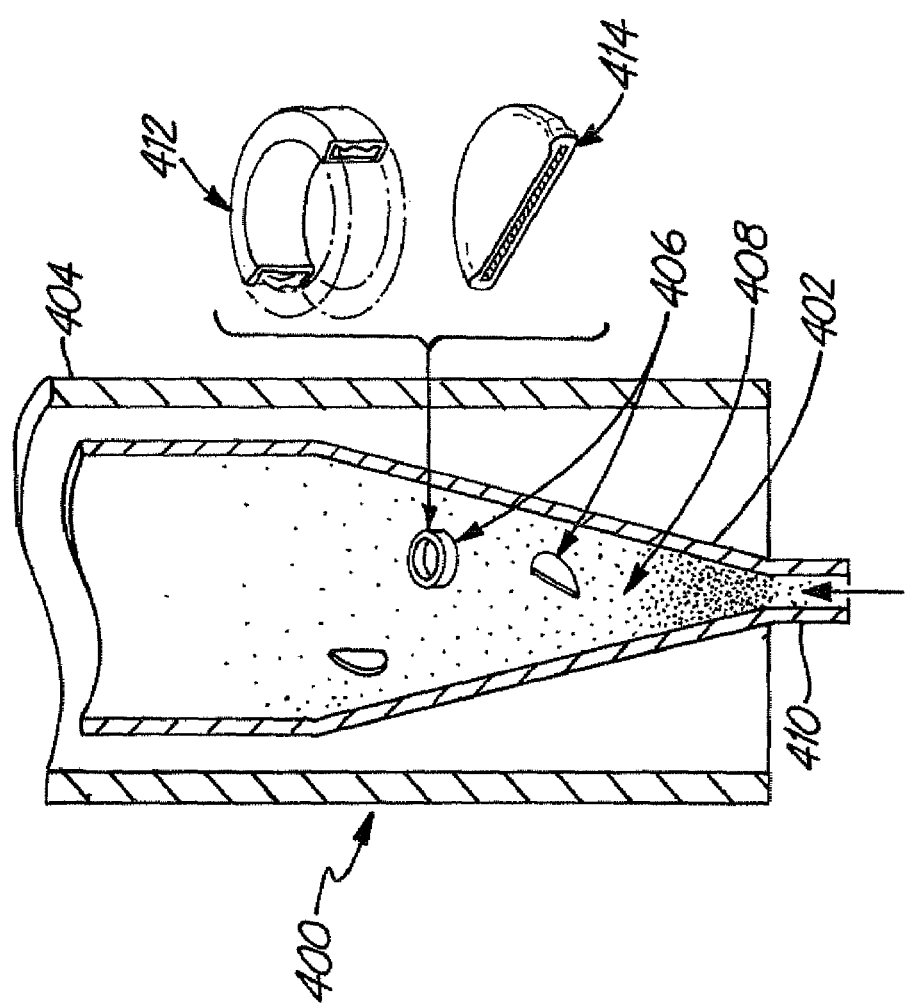

PYROLYTIC CARBON AND METAL/METALLOID CARBIDE COMPOSITES

BACKGROUND OF THE INVENTION

The invention relates to medical devices (articles) formed from improved materials that include pyrolytic carbon as a component of a composite. In particular, the invention relates to medical devices that incorporate improved composite materials including a pyrolytic carbon component and a metal/metalloid carbide component.

A variety of medical devices are designed particularly for contact with a patient's bodily fluids. The duration of this contact may be relatively short, as is typical with surgical instruments, or may be long term, as is typical with prosthetic heart valves implanted into the body of a recipient, and other implanted prostheses. Some devices, such as catheters, can have either short term or relatively long term contact.

Prostheses, i.e., prosthetic devices, are used to repair or replace damaged or diseased organs, tissues and other structures in humans and animals. Prostheses generally must be biocompatible since they are typically implanted for extended periods of time. Examples of prostheses include, without limitation, prosthetic hearts, prosthetic heart valves, ligament repair materials, vessel repair and replacement materials, stents, and surgical patches.

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a mechanical or bioprosthetic, i.e., tissue based, valve. Another technique uses an annuloplasty ring to provide structural support to the natural annulus of the native valve. Annuloplasty rings can also be used with prosthetic heart valves.

Many biocompatible medical devices and/or their components have significant requirements with respect to their mechanical and physical properties. For example, the medical devices are often limited in their size. At the same time, the devices and/or their components may be subjected to demanding performance requirements, such as mechanical strength and long term durability. Thus, there are significant restraints imposed on the design of many medical devices and/or their components.

As a particular example, mechanical heart valve prostheses include an orifice ring with one or more occluders. Commonly, mechanical valve occluders consist of two thin hemidiscs called leaflets, but other occluders include thick discs and balls. Heart valve occluders/leaflets perform the function of opening and closing to regulate the blood flow through the heart valve. Heart valve occluders typically pivot with each cycle of a pumping heart to open and close the valve at appropriate times. The heart valve prosthesis should provide good hemodynamic performance. In addition, the valve should be durable to provide stable performance over many years of use.

While mechanical valves generally provide important clinical benefits, these benefits are counterbalanced by the need for anticoagulation therapy and the associated risks of anticoagulant bleeding due to such therapy. Another limitation with some mechanical valves is a residual transvalvular pressure difference across the open valve that is larger than the pressure difference for a healthy native valve. An excessive transvalvular pressure difference imposes an extra workload on the patient's heart that may contribute to disease in cardiac tissue. Pyrolytic carbon is a preferred material for mechanical heart valves because of its relatively high thromboresistance and its durability. However, there are limitations in the shape and thicknesses of valve components made from pyrolytic carbon because it is a brittle material with moderate strength. These shape and thickness limitations may result in higher than desired transvalvular pressure differences.

In addition, a variety of other medical devices, such as orthopedic prostheses and dental implants, can advantageously be formed with pyrolytic carbon. Orthopedic prostheses can be used for hard tissue replacement, bone replacement and joint replacement. Similarly, a variety of dental implants are used to replace teeth due to loss from dental decay or disease. The material properties of pyrolytic carbon may impose limitations on the use of pyrolytic carbon for these other applications.

SUMMARY OF THE INVENTION

In a first aspect, the invention pertains to a medical device including a carbon-containing material that has at least two compositions. The first composition includes at least about 50 percent by volume pyrolytic carbon while the second composition includes at least about 80 percent by volume of a metal carbide or metalloid carbide (hereinafter "carbide") composition.

In another aspect, the invention pertains to a method of producing an improved material for a medical device. The method includes a step of depositing two compositions over a substrate. The first composition includes at least about 50 percent by volume pyrolytic carbon, and the second composition includes at least about 80 percent by volume of a carbide composition.

In a further aspect, the invention pertains to a medical device including a carbon-containing material with an inner layer. In particular, the carbon-containing material has an inner layer with at least about 50 percent by volume of a carbide composition.

The invention also pertains to a medical device including a carbon-containing material with at least two different compositions. The carbon-containing material consists essentially of a first composition including at least about 50 percent by volume carbide and a second composition including at least about 50 percent by volume pyrolytic carbon.

In addition, the invention pertains to a heart valve prosthesis comprising a graphite substrate having a coating over at least a portion of its surface. The coating has a first layer adjacent the substrate of at least about 50 percent by volume pyrolytic carbon and less than about 50 percent by volume carbide composition. A second layer adjacent the first layer has at least about 50 volume percent carbide composition. A third layer adjacent the second layer has at least about 50 volume percent pyrolytic carbon and no more than about 50 volume percent carbide composition. A surface layer adjacent the third layer includes at least about 80 volume percent pyrolytic carbon.

BRIEF DESCRIPTION OF THE DRAWINGS

FIG. 10 is a fragmentary, sectional side view of a preferred embodiment of the composite material, where the cross section is taken to expose the layering of the composite material.

FIG. 11 is a fragmentary, sectional side view of an alternative preferred embodiment of the composite material, where the cross section is taken to expose the layering of the composite material.

FIG. 13 is a schematic, sectional view of a fluidized bed reactor, with an exploded sectional view of a heart valve prosthesis for coating, where the cross section is taken vertically approximately through the center of the respective reactor or component.

DETAILED DESCRIPTION OF THE ILLUSTRATIVE EMBODIMENTS

Figure 1:
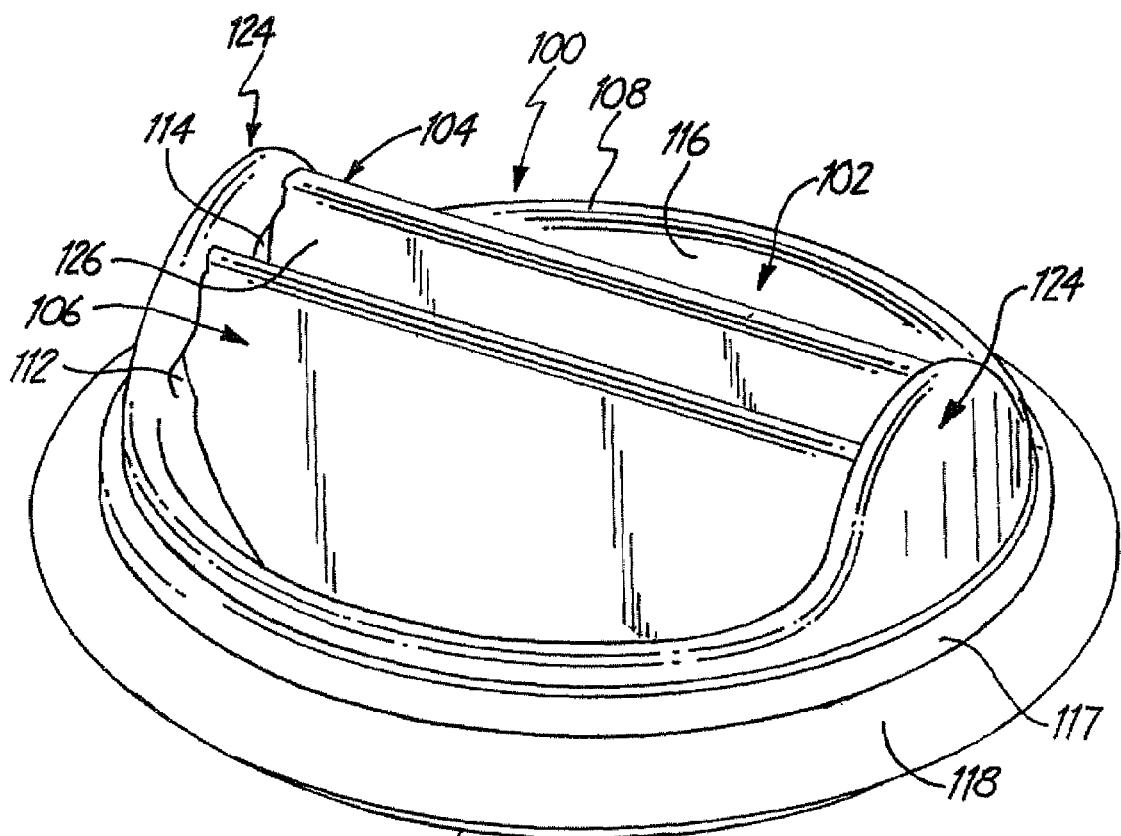
FIG. 1 is a perspective view of a bi-leaflet mechanical heart valve prosthesis with occluders and an orifice ring.

Medical devices can be constructed from improved composite materials that include at least one layer of metal/metalloid carbide, hereinafter "carbide", or an alloy of pyrolytic carbon and metal/metalloid carbide that provides structural strength to the composite material. The composite materials also include one or more layers of pyrolytic carbon. Layers containing a majority of metal/metalloid carbide can be located at the surface of the composite or within the interior of the composite. The carbon microstructure can be modified to improve structural performance.

Due to the structural support contributed by the carbide composition, a thinner composite material can be used while maintaining a desirable degree of mechanical strength and durability. Thus, a material is available with the blood compatibility of pyrolytic carbon but with improved mechanical properties. Such improvements in mechanical properties enable the fabrication of more hemodynamic, thinner shapes for medical devices, such as mechanical valve components and corresponding heart valves.

These composite materials are particularly suitable for the production of medical articles, especially medical articles that contact a patient's bodily fluids and/or tissues. These biocompatible medical articles generally incorporate a biocompatible material, which is intended to contact the patient's bodily fluids and/or tissues. Bodily fluids include, for example, blood, plasma, serum, interstitial fluids, saliva and urine. The patient can be an animal, especially a mammal, and preferably is a human.

Relevant medical articles include devices that contact a person's bodily fluids and/or tissues for varying lengths of time, for example, prostheses. Prostheses, i.e., prosthetic articles, are used to repair or replace damaged or diseased organs, tissues and other structures in humans and animals. Prostheses generally must be biocompatible since they are typically implanted for extended periods of time. Preferred prostheses include prostheses used in the cardiovascular and vascular system in which the properties of the surface in contact with blood flow are important to the biocompatibility and durability of the prostheses. Other preferred prostheses include orthopedic prosthetic implants, such as replacement bones and joints, as well as dental implants.

Materials used in the production of medical devices, especially implantable prostheses and other devices that contact a patient's bodily fluids and/or tissues, have particular requirements for their properties. The materials should be biocompatible. Biocompatible materials are non-toxic, effectively non-carcinogenic and do not induce hemolysis or a significant immunological response. Medical devices used to contact bodily fluids and tissues preferably are formed from non-thrombogenic materials. Furthermore, in many applications, the materials should have desirable mechanical properties, such as elasticity or stiffness, strength, fatigue resistance, wear resistance and fracture toughness, without introducing excessive weight or bulk.

Graphite is a crystalline form of carbon having $sp^2$ bonding, in which the covalently bonded carbon forms sheets that interact by relatively weak interactions. Pyrolytic carbon is a form of carbon that is related to graphite in having generally $sp^2$ bonding of carbon atoms. In contrast with graphite, pyrolytic carbon lacks long-range crystalline order. Pyrolytic graphite is a form of carbon having crystalline order greater than that of pyrolytic carbon, although sometimes less than that of crystalline graphite. Unlike graphite and pyrolytic graphite, pyrolytic carbon is isotropic with respect to macroscopic properties; in other words, it has essentially uniform properties including, for example, mechanical strength, in all directions. The structure of pyrolytic carbon is referred to as "turbostratic" to indicate its disordered and jumbled nature.

The pyrolytic carbon for formation of the composite materials can be formed by processes such as chemical vapor deposition or variants of chemical vapor deposition including, for example, plasma enhanced or plasma assisted chemical vapor deposition. The pyrolytic carbon is deposited onto a substrate material. In some embodiments, the substrate is removed, for example, by grinding or other mechanical methods, subsequent to deposition of the pyrolytic carbon. Carbides and carbide—pyrolytic carbon alloys can also be deposited by chemical vapor deposition approaches, as described further below.

Various carbon-based materials have been used in the production of medical devices due to advantageous properties. For example, graphite is a useful substrate for pyrolytic carbon due to its relative strength and ease of manufacture. Pyrolytic carbon is useful due to desirable thromboresistance and generally high durability. Thus, pyrolytic carbon can be used as a coating for medical articles that contact a patient's bodily fluids and tissues. The pyrolytic carbon can include amounts of carbide compounds to improve the mechanical properties of the device. The pyrolytic carbon of the composites described herein generally are located within one or more layers of pyrolytic carbon.

The use of a layer that is a majority carbide, i.e., metal carbide and/or metalloid carbide, can be used to form new composite materials that have desirable levels of mechanical strength, stiffness and increased toughness when formed into very thin structures. Metalloids are elements that exhibit chemical properties intermediate between or inclusive of metals and nonmetals. Metalloid elements include silicon, boron, arsenic, antimony, and tellurium. The metal/metalloid carbide layer(s) generally includes an alloy of one or more carbide compounds with pyrolytic carbon, although the layer can be almost pure carbide, about 99 percent by weight carbide. The metal/metalloid carbide layer generally has greater than about 50 percent by volume metal/metalloid carbide. While the metal/metalloid carbide generally is in an alloy with pyrolytic carbon, the metal/metalloid carbide can be essentially pure carbide. The carbide/pyrolytic carbon alloy generally is formed by codeposition. The resulting carbide/pyrolytic carbon alloy includes grains of the two materials in close contact with each other.

One or more layers of the carbide compound is incorporated into a composite material that can also include one or more layers of pyrolytic carbon/carbide alloy transition layers. The transition layers generally have intermediate amounts of carbide and are placed between a layer of carbide and a layer of pyrolytic carbon, although the invention covers structures with more complex variation in composition through the material. Transition layers provide increased durability and mechanical stability with respect to inhibiting delamination of the layers. Such potential delamination could occur during cool-down following chemical vapor deposition at an elevated temperature. In preferred embodiments, a pyrolytic carbon layer is located at the surface of the material due to the desirable blood compatibility properties of pyrolytic carbon and an ability to utilize current manufacturing process technology, such as machining and surface finishing.

In alternative embodiments, the composition of the composite effectively varies continuously throughout the composite, such that there are no identifiable layers. For example, the proportion of pyrolytic carbon and carbide compounds can vary according to depth within the composite. For instance, the surface of the continuously varying composite can include a majority of pyrolytic carbon while inner regions of the composite can include a majority of carbide.

The composite materials generally are formed with one or more materials added as a coating onto a substrate or preform. In some embodiments, the substrate provides additional mechanical strength to the composite. In these embodiments, substrates adhere strongly to the coating applied over the substrate. In some preferred embodiments, the substrate is removed after the coating process, such that a thinner and lighter structure of the composite material is formed, and strong adhesion of the coating is not essential. In these embodiments without a substrate, the composite comprises solely layers or gradients of both pyrolytic carbon and metal/metalloid carbides.

The composites described herein can have higher stiffness, i.e., a higher Young's modulus of elasticity, than pyrolytic carbon materials. Similarly, the composites can have a reduced brittleness as measured by a higher fracture toughness. Since thinner materials can be formed with desirable levels of stiffness, increased strength, and increased toughness, improved medical devices can be formed. For example, orifice rings of mechanical heart valves can be formed with an increased effective orifice area due to a decreased wall thickness. In addition, more hemodynamic shapes can be formed without increasing the thickness or weight of the device components to undesirable levels. In addition, these composite materials can be useful materials for the formation of orthopedic medical devices, such as finger joints, and dental implants, such as tooth replacements.

Medical Articles

Relevant biocompatible articles include all medical articles that contact bodily fluids and/or tissues and are generally rigid or stiff. These articles can be organized roughly into three groups: implanted devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a wound site or at a moist membrane, such as within a patient's mouth.

Implanted medical devices include, without limitation, prostheses such as pacemakers, defibrillators, artificial organs such as artificial hearts, ventricular assist devices, anatomical reconstruction prostheses such as jaw implants, heart valve prostheses, surgical patches or plates, coronary stents, vascular, cardiovascular and structural stents, vascular and cardiovascular shunts, pledgets, annuloplasty rings, stents, staples, connectors, electrical leads such as pacing leads, valved grafts, orthopedic or spinal implants, orthopedic pins, intrauterine devices (IUDs), urinary stents, permanently indwelling percutaneous devices, maxial facial reconstruction plating, dental implants, clips, bone, orthopedic prostheses, and combinations thereof.

Percutaneous medical devices include, without limitation, cannulas, introducers, and drainage tubes such as chest tubes. Desired coatings can reduce friction of percutaneous devices. Cutaneous medical devices include, without limitation, dental hardware, such as bridge supports and bracing components.

While the pyrolytic carbon—carbide composites can be used in any of the medical articles described above, a few medical devices are of particular interest. Such devices of particular interest include, for example, vascular stents, such as coronary stents, ventricular assist devices with or without valves, and valved cardiovascular prostheses, such as heart valve prostheses, valved grafts, and artificial hearts. The composite materials are particularly suitable for use as orifice rings or rigid occluders in heart valve prostheses.

A bi-leaflet mechanical heart valve prosthesis 100 is shown in FIG. 1. Heart valve prosthesis 100 includes an orifice ring 102 which retains two occluders 104, 106. Orifice ring 102 has an upstream surface 108 and a downstream surface 110. Occluders 104, 106 rotate at pivots 112, 114 and two additional opposed pivots symmetrically positioned on the inner surface 116 of orifice ring 102 (not shown). Inner luminal surface 116 of orifice ring 102 forms a flow path through the valve that can be opened or closed through the pivoting of occluders 104, 106. A sewing cuff 118 is placed around orifice ring 102 to facilitate attachment with the patient's tissue during implantation of the valve. In the embodiment shown in FIG. 1, an orifice ring 102 has a pivot guard structure 124, which projects upstream of the plane of orifice ring 102.

Blood flows through the prosthesis in an effectively unidirectional way. Occluders 104, 106, shown in the open position in FIG. 1, pivot in response to forces imparted by the blood during the cardiac cycle. Occluders 104, 106 cyclically close to effectively block back flow through the valve lumen. In the closed position, downstream surfaces of occluders 104, 106 block back flow through the valve. Downstream surface 126 of occluder 104 is shown in FIG. 1. Occluders 104, 106 subsequently assume an open position to allow forward flow through the valve lumen.

All or a portion of occluders 104, 106 can be formed from a pyrolytic carbon-carbide composite material. In addition, all or a portion of ring 102 can be formed from a pyrolytic carbon-carbide composite. Inner luminal surface 116 preferably includes a majority component of pyrolytic carbon. In some preferred embodiments, ring 102 is formed from a pyrolytic carbon-carbide composite without a substrate such that ring 102 is particularly thin. In some embodiments, the material at the exterior surface 117 of orifice ring 102 has a composition including metal/metalloid carbide.

Figure 2:
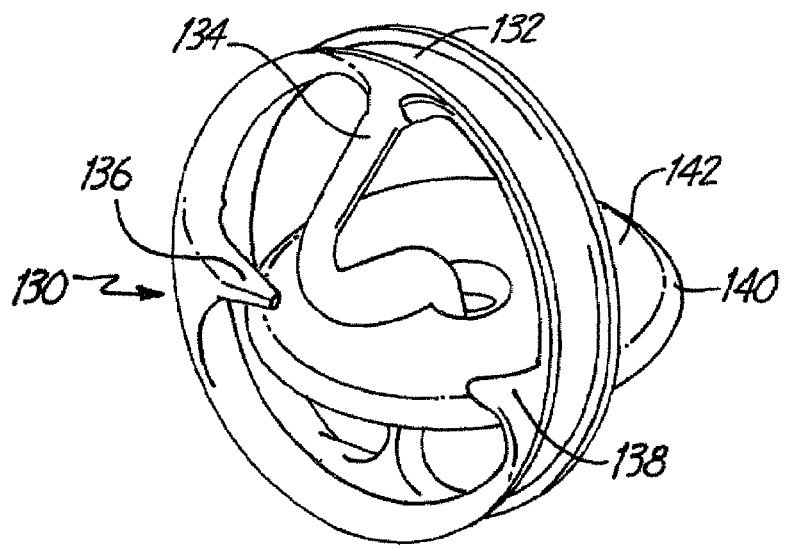
FIG. 2 is a perspective view of a single occluder mechanical heart valve prosthesis with an occluder and orifice ring.

The composite materials can be used to form different embodiments of mechanical heart valves. For instance, a single-occluder mechanical heart valve prosthesis 130 is shown in FIG. 2. Heart valve prosthesis 130 includes an orifice ring 132 with a pivot arm 134 and two stops 136, 138. Occluder 140 can swing on pivot arm 134 to move between a closed position, and an open position, as shown in FIG. 2. At a fully open position, the swinging motion of occluder 140 is halted by stops 136, 138. Orifice ring 132 and/or occluder 140 can be formed from pyrolytic carbon-carbide composites. Similarly, portions of the components can be formed from the composites. Blood flow through valve 130 is effectively unidirectional such that the valve closes with downstream surface 142 of occluder 140 blocking back flow through the valve.

Figure 3:
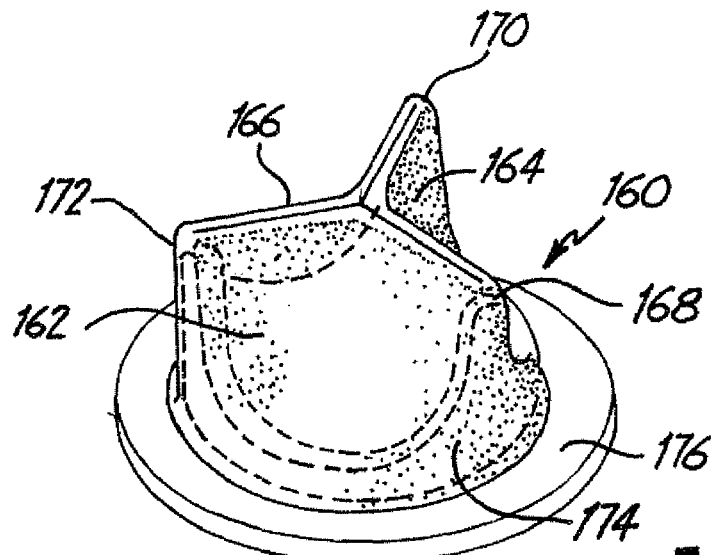
FIG. 3 is a perspective view of a heart valve prosthesis having flexible polymer leaflets connected to a stent.

An embodiment of a heart valve prosthesis with flexible polymer leaflets or occluders is shown in FIG. 3. Heart valve prosthesis 160 includes leaflets 162, 164, 166 joined at commissures 168, 170, 172. Sewing ring 176 is used to attach valve 160 to patient tissue. Leaflets 162, 164 and 166 and sewing ring 176 are attached or adhered to and supported by stent 174 (shown in phantom). While the heart valve prosthesis in FIG. 3 is shown with three polymer leaflets, prostheses can be constructed with different numbers of polymer leaflets, such as two leaflets. Flexible leaflets can also be produced from tissue, such as bovine pericardium. Stent 174 or a portion thereof can be formed using the pyrolytic carbon/carbide composites.

Biocompatible Materials

Relevant medical articles can include one or more biocompatible materials. The medical devices of interest include at least a component comprising the pyrolytic carbon-carbide composite materials described herein. The medical devices may include, in addition to the pyrolytic carbon-carbide composites, other biocompatible materials, such as tissue or tissue-derived material, polymers, metals, pyrolytic carbon, graphites, ceramics and combinations thereof. Any of these other materials can be a separate material within the same component as the pyrolytic carbon-carbide composite, or these other material(s) may be in distinct components that are joined with the other components to form the completed medical article.

In particular, appropriate biocompatible materials in addition to the pyrolytic carbon/carbide composites can be formed from natural materials, synthetic materials or combinations thereof. Natural, i.e., biological, material for use in the invention includes relatively intact living tissue, decellularized tissue and recellularized tissue. These tissues may be obtained from, for example, native heart valves, portions of native heart valves or cardiac tissues such as aortic roots, walls and leaflets, pericardial tissues, such as pericardial patches, connective tissues, tendons, ligaments, skin patches, blood vessels, cartilage, dura mater, skin, bone, fascia, submucosa, umbilical tissues, and the like.

Natural tissues are derived from a selected animal species, typically mammalian, such as human, bovine, porcine, seal, equine, canine or kangaroo. These natural tissues generally include collagen-containing material. Tissues can be fixed by crosslinking. Fixation provides mechanical stabilization, for example, by preventing enzymatic degradation of the tissue. Glutaraldehyde or formaldehyde is typically used for fixation, but other fixatives can be used, such as other difunctional aldehydes, epoxides, genipin and derivatives thereof.

Relevant synthetic materials in addition to the pyrolytic carbon/carbide composites include, for example, polymers, metals, carbonaceous solids and ceramics. Ceramics are intended to have a broad meaning in terms of high melting temperature solids including metal and/or silicon compounds. Appropriate ceramics include, for example, hydroxyapatite and alumina. Relevant carbonaceous solids include, for example, graphite and pyrolytic carbon. Ceramics can be coated with a polymer, protein or other compound prior to use, if desired. Suitable inert metals include, for example, titanium, cobalt, stainless steel, nickel, iron alloys, cobalt alloys, such as Elgiloy®, a cobalt-chromium-nickel-molybdenum-iron alloy, and MP35N, a nickel-cobalt-chromium-molybdenum alloy, and Nitinol®, a nickel-titanium alloy. Appropriate synthetic materials also include hydrogels and other synthetic materials that cannot withstand severe dehydration.

Biocompatible polymer materials can be fabricated from synthetic polymers as well as purified biological polymers. These synthetic polymeric materials can be formed into fibers and/or yarn and then woven or knitted into a mesh to form a matrix or similar structure. Alternatively, the synthetic polymer materials can be molded, extruded, dip coated or cast into appropriate forms.

Appropriate synthetic polymers include, for example, polyamides (e.g., nylon), polyesters, polystyrenes, polyacrylates, vinyl polymers (e.g., polyethylene, polytetrafluoroethylene, polypropylene and polyvinylchloride), polycarbonates, polyurethanes, poly dimethyl siloxanes, cellulose acetates, polymethyl methacrylates, ethylene vinyl acetates, polysulfones, polyacetals, nitrocelluloses and similar copolymers. Other suitable polymers include resorbable polymers such as dextran, hydroethyl starch, derivatives of gelatin, polyvinylpyrrolidone, polyvinylalcohol, poly[N-(2-hydroxylpropyl) methacrylamide], polyglycols, polyesters, poly(orthoesters), poly(ester amides), and polyanhydrides. Resorbable polyesters include, for example, poly(hydroxy acids) and copolymers thereof, poly(ε-caprolactone), poly (dimethyl glycolic acid), and poly(hydroxy butyrate). Preferred resorbable polymers include, for example, D, L-polylactic acid, L-polylactic acid, poly(glycolic acid), and copolymers of L-lactic acid, D-lactic acid and glycolic acid. For example, sewing cuff 118 of bi-leaflet heart valve prosthesis 100 of FIG. 1 can be formed to include a resorbable fabric.

Biological polymers can be naturally occurring or produced in vitro by fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, cat gut sutures, polysaccharides (e.g., cellulose and starch) and copolymers thereof.

Composite Structure

Figure 4:
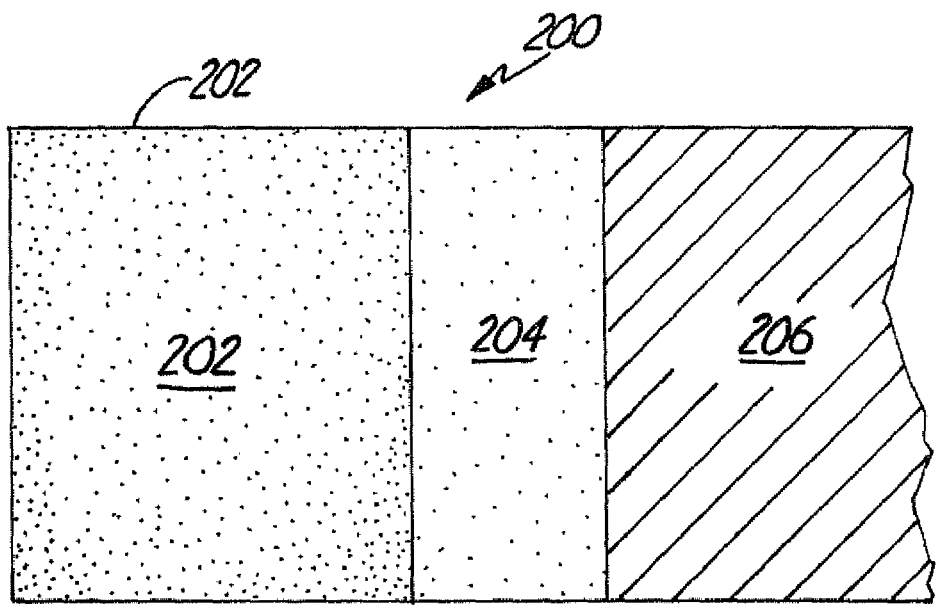
FIG. 4 is a fragmentary, sectional side view of an embodiment of a composite of the invention, where the cross section is taken to expose the layering of the composite material.

The pyrolytic carbon-carbide composite materials include, at least, a portion of the material that includes a majority of pyrolytic carbon and another portion that includes a majority of a carbide composition. The carbide composition can be a metal carbide, such as titanium carbide, tungsten carbide, tantalum carbide and zirconium carbide, a metalloid carbide, such as silicon carbide or boron carbide, or a combination thereof. A cross section of a simple layered embodiment of the composite is shown in FIG. 4. Composite 200 has a carbide layer 202 on the outer surface, a pyrolytic carbon layer 204 and an optional substrate 206. For certain embodiments, a substrate is used to form the material, and the substrate is subsequently removed to form a substrateless composite.

Typically, a substrate is needed to form the composite since carbide layer 202 and pyrolytic carbon layer 204 generally are deposited by vapor deposition methods that require the presence of a substrate. Suitable substrates include, for example, graphites, refractory metals and refractory ceramics. The substrate, however, can be removed subsequent to the formation of the carbide, pyrolytic carbon and/or alloy layers, as described further below. Graphite is a preferred substrate for subsequent removal since it can be readily abraded. Also, graphite is a preferred substrate for the deposition of pyrolytic carbon because of the similar coefficients of thermal expansion.

Figure 5:
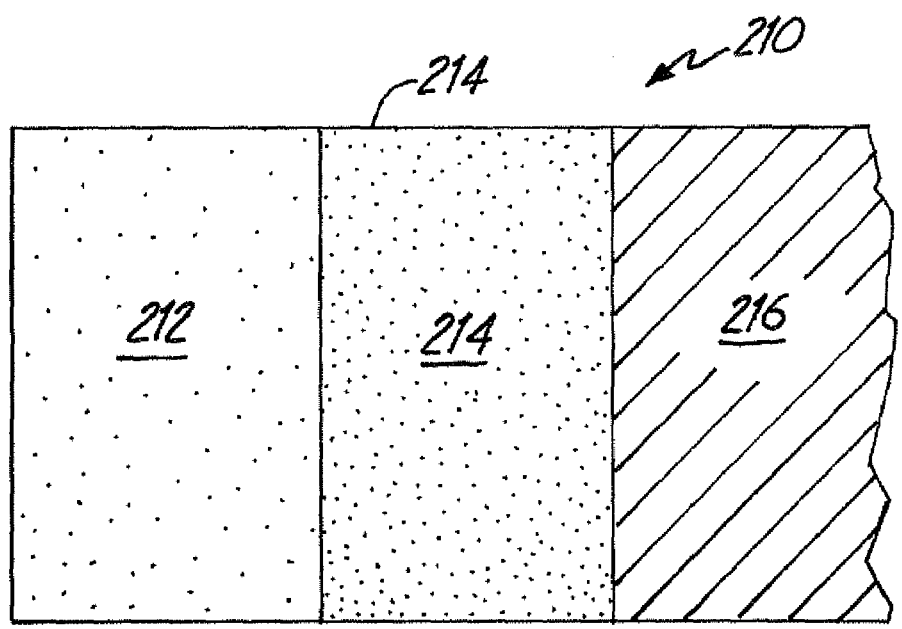
FIG. 5 is a fragmentary, sectional side view of an alternative embodiment of a composite of the invention, where the cross section is taken to expose the layering of the composite material.

Referring to FIG. 5, an alternative embodiment of the composite 210 is shown. Pyrolytic carbon layer 212 is on the outer surface of the composite, adjacent to carbide layer 214. Carbide layer 214 is in contact with substrate 216.

Figure 6:
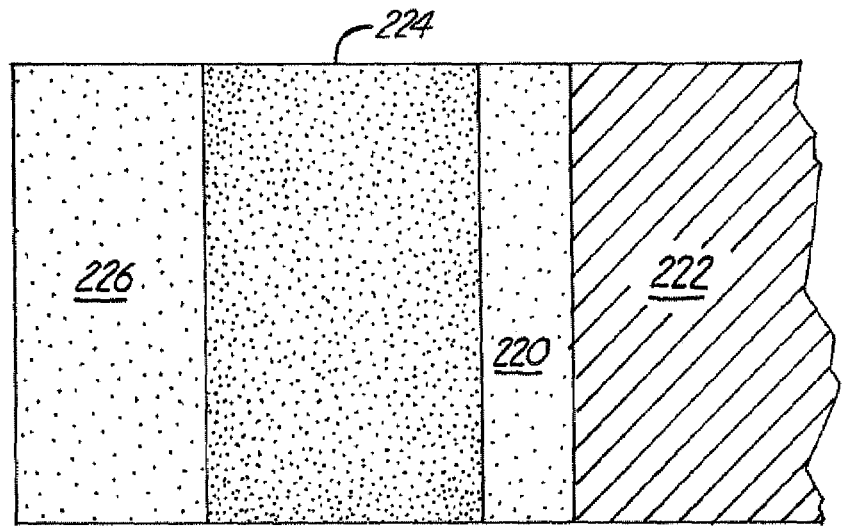
FIG. 6 is a fragmentary, sectional side view of an embodiment of the composite material with three layers of material on a substrate surface, where the cross section is taken to expose the layering of the composite material.

Three layers deposited on a substrate are depicted in FIG. 6. Pyrolytic carbon layer 220 is deposited adjacent substrate 222. Carbide layer 224 is located between pyrolytic carbon layer 220 and pyrolytic carbon layer 226.

Figure 7:
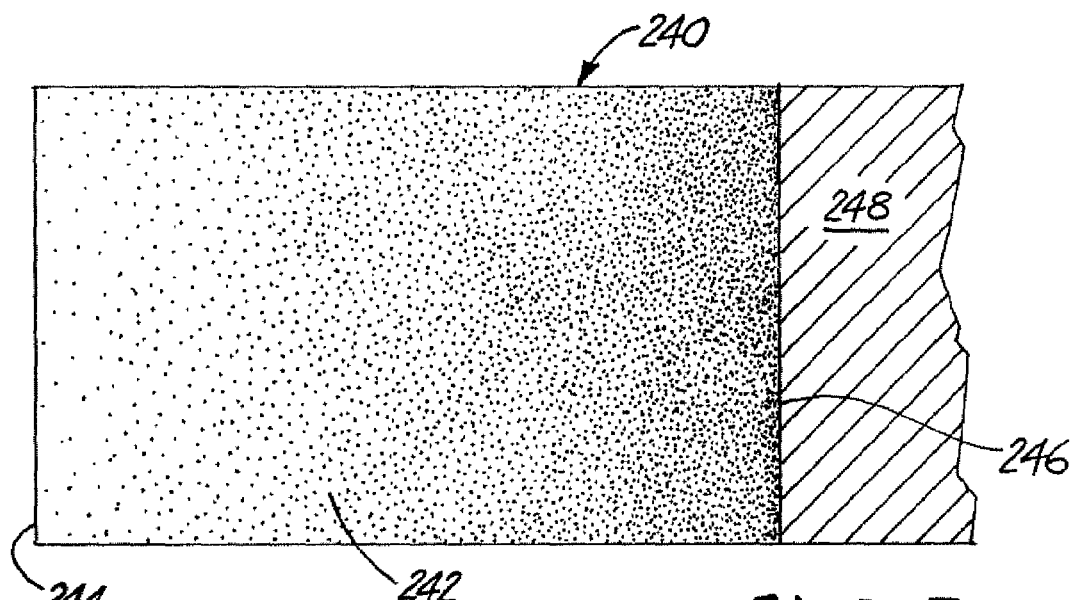
FIG. 7 is a fragmentary, sectional side view of an embodiment of the composite material with a composition gradient layer, in which an optional substrate is depicted at a pyrolytic carbon edge of the gradient layer, where the cross section is taken to expose the layering of the composite material.
Figure 8:
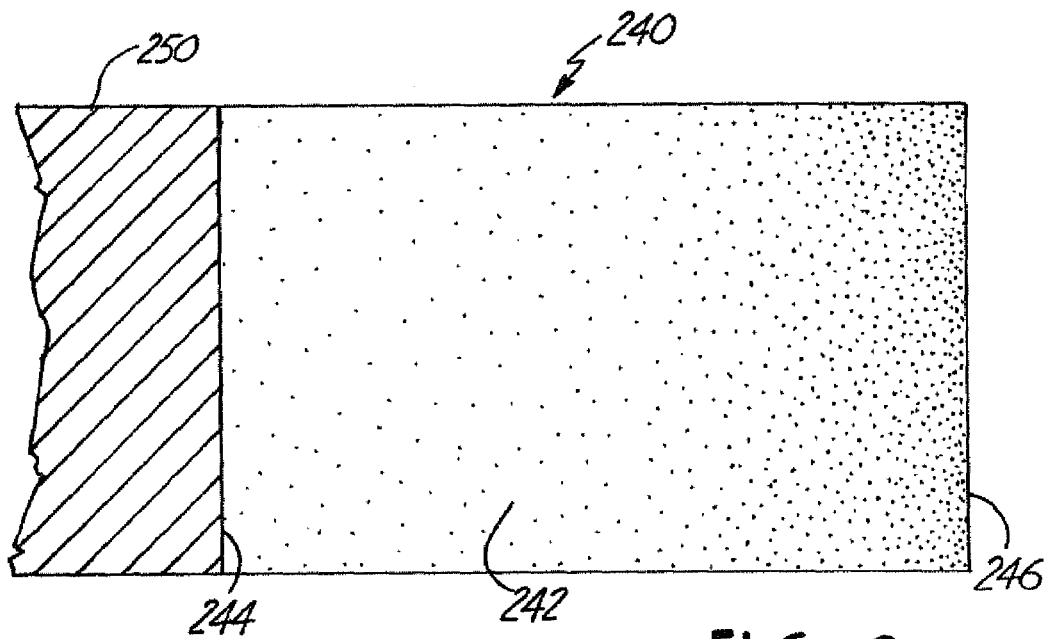
FIG. 8 is a fragmentary, sectional side view of an embodiment of the composite material with a composition gradient layer, in which an optional substrate is depicted at a carbide edge of the gradient layer, where the cross section is taken to expose the layering of the composite material.

As noted above, the composites of interest include an identifiable portion with a majority composition of pyrolytic carbon and a distinct, identifiable portion with a majority composition of carbide. These materials do not need to be in discrete layers, however. In some embodiments, the composition of the material changes effectively continuously along one dimension through the thickness of the composite material. Such an embodiment is shown schematically in cross section in FIG. 7. Composite 240 includes a material 242 with a gradient in composition from a majority pyrolytic carbon at surface 244 to a majority carbide at surface 246. The continuous gradient in composition of this transition or gradient layer is indicated pictorially by the variation in marking across material 242. Optional substrate 248 is shown adjacent surface 246. Optional substrate 250 is shown adjacent surface 244 of material 242 in FIG. 8, such that carbide is on the surface. The gradient in composition does not have to be monotonic, and the composite can include multiple, separated regions within material 242 with a majority of pyrolytic carbon and/or a majority of metal/metalloid carbide.

In addition, the composite material can include one or more layers of material with a composition gradient. Gradient layers can be used as transition layers between other layers to produce a more stable composite. In particular, a transition layer with a composition gradient can be used to reduce or eliminate composition differences at interfaces or to produce composition differences at interfaces that are mechanically and/or thermally stable. For example, a gradual transition in coefficient of thermal expansion, which can be achieved by creating a gradual transition in composition, may be desirable for stability of the coating layers under changing thermal conditions. Such changing thermal conditions occur, for example, during the period immediately after completing the coating process, during which the material returns to room temperature from an elevated coating temperature. Thus, the possibility of delamination, i.e., separation of different layers, can be reduced or effectively eliminated using transition layers with composition gradients. For the production of substrateless materials, it may be desirable to have delamination of the composite from the substrate.

Figure 9:
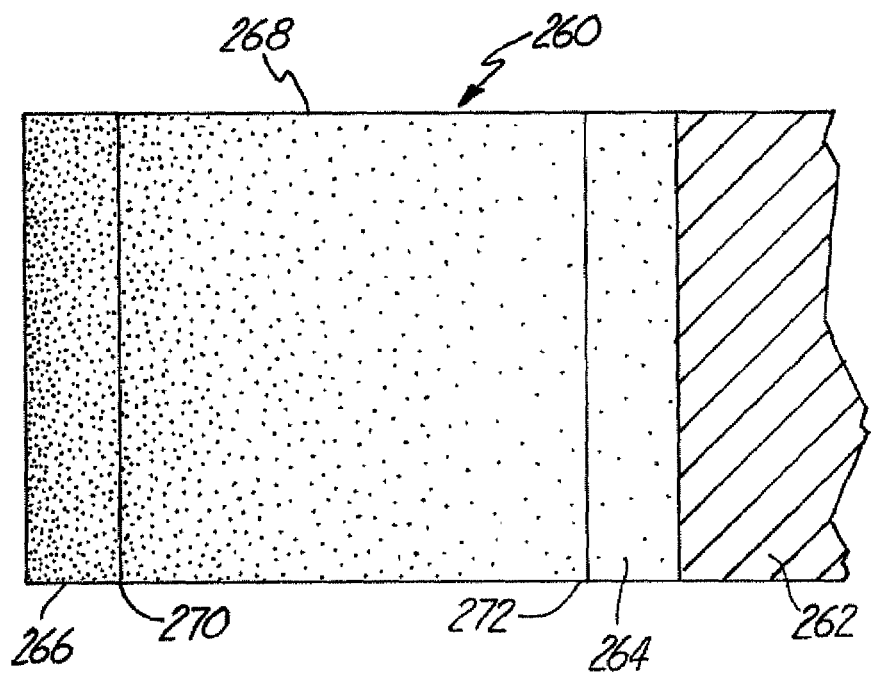
FIG. 9 is a fragmentary, sectional side view of an embodiment of the composite material having a gradient layer located between layers with different compositions, where the cross section is taken to expose the layering of the composite material.

One embodiment of a composite 260 with a layer having a composition gradient is depicted in FIG. 9. Composite 260 includes an optional substrate 262, an adjacent pyrolytic carbon layer 264, and an outer carbide layer 266. Gradient layer 268 is located between pyrolytic carbon layer 264 and carbide layer 266. Gradient layer 268 has an interface plane or a interface layer 272 with a pyrolytic carbon composition having a composition that is the same as or similar to pyrolytic carbon layer 264. An interface layer within a gradient layer is a thin layer adjacent to an interface with a layer of approximately constant composition. Similarly, gradient layer 268 has an interface layer 270 with a composition that is the same as or similar to carbide layer 266. In this embodiment, the composition varies monotonically along the gradient between interface layers 270 and 272, although the rate of change with distance along the gradient does not have to be constant. The embodiment lacking optional substrate 262 has the advantage of being a thinner material assuming that the other layers are unchanged. Embodiments with thinner components can be an advantage for certain applications, as described herein. Also, in the embodiments lacking optional substrate 262, instability of the interface between substrate 262 and pyrolytic carbon layer 264 may be advantageous for substrate removal.

Different embodiments of the composite material can be formed using a variety of alternative layer compositions and order of layers. In preferred embodiments, gradient layers are used to preclude abrupt compositional changes at layer interfaces. In embodiments incorporating appropriate layer compositions and gradient layers as transition layers, a very stable and durable composite material is formed. Unless the materials have clearly distinguishable appearances, interfaces may not be visibly identifiable to the unaided eye. However, layers, interfaces and transitions may be identifiable by chemical analysis methods applied to sectional composite material as well as by a review of the deposition protocol.

One particularly preferred embodiment is composite 280, as depicted in FIG. 10. In composite 280, a substrate 282 is located in the interior of the material. Gradient layers 284, 286 are located on the respective, opposite sides of substrate 282. Gradient layers 284, 286 have pyrolytic carbon adjacent substrate 282. Carbide layers 288, 290 are located adjacent gradient layers 284, 286, respectively. Gradient layers have carbide layers 292, 294 adjacent carbide layers 288, 290.

To introduce desirable surface properties to the composite, pyrolytic carbon layers 296, 298 are located at the outer surfaces of composite 280. Gradient layers 300, 302 are located between carbide layers 288, 290 and pyrolytic carbon layers 296, 298, respectively. Gradient layers 300, 302 have carbide interface layers 304, 306 adjacent carbide layers 288, 290, respectively, and pyrolytic carbon interface layers 308, 310 adjacent pyrolytic carbon layers 296, 298, respectively.

A variation of the embodiment of FIG. 10 is shown in FIG. 11. Composite material 320 of FIG. 11 has pyrolytic carbon layers 322, 324 adjacent substrate 326. Gradient layers 328, 330 are located adjacent pyrolytic carbon layers 322, 324, respectively. Gradient layers 328, 330 have pyrolytic carbon interface layers 332, 334 adjacent pyrolytic carbon layers 322, 324, respectively. Gradient layers 328, 330 are analogous to gradient layers 284, 286 of composite material 280 shown in FIG. 10. The layers of composite 320 on the outside of gradient layers 328, 330 are the same as or similar to corresponding layers 288, 290, 296, 298, 300, 302 on the outside of gradient layers 284, 286 of composite 280.

Figure 12:
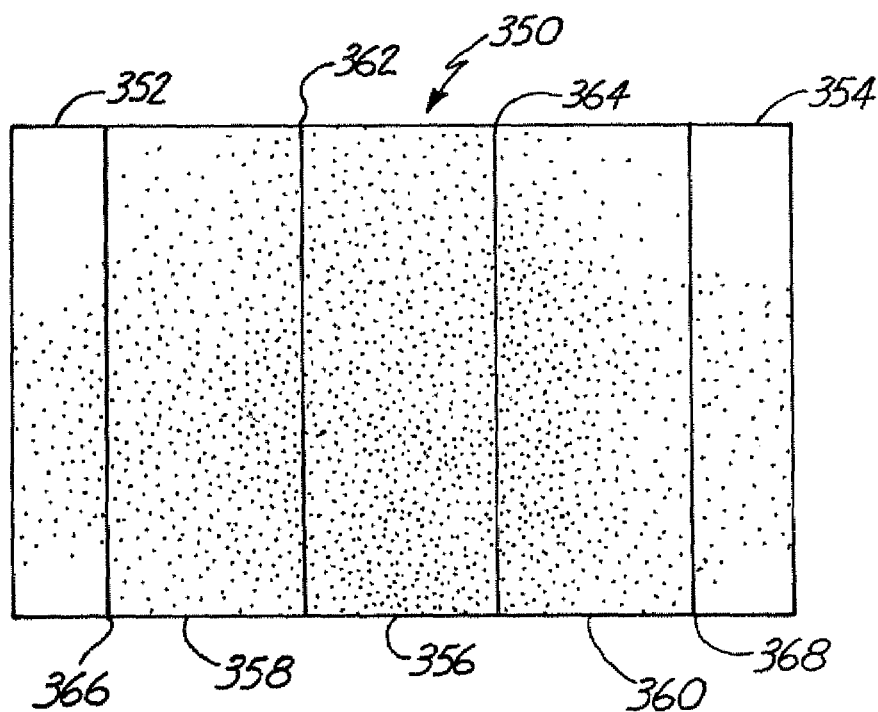
FIG. 12 is a fragmentary, sectional side view of another alternative preferred embodiment of the composite material, where the cross section is taken to expose the layering of the composite material.

Another preferred embodiment of the invention is composite 350, as depicted in FIG. 12. Composite 350 has pyrolytic carbon layers 352, 354 at the outer surfaces. Carbide layer 356 is located in the interior of composite 350. Gradient layers 358, 360 are located between carbide layer 356 and pyrolytic carbon layers 352, 354, respectively. Gradient layers 358, 360 have carbide interface layers 362, 364 adjacent carbide layer 356 and pyrolytic carbon interface layers 366, 368 adjacent pyrolytic carbon layers 352, 354, respectively. While the embodiments shown in FIGS. 10-12 generally are preferred embodiments, some simpler embodiments may be preferred, if they have sufficient thermal stability, due to cost savings and ease of production.

Preferred embodiments 280, 320, 350 of the composite materials have pyrolytic carbon at their outer surfaces due to desirable surface properties of these materials. In addition, the inner and outer layers of preferred embodiments can be selected to enhance the ability to manufacture the medical device using conventional processing technology. While some improved composite materials may possess improved mechanical properties, these materials may have disadvantages in terms of manufacturing inefficiencies. Therefore, an inner layer may be selected to improve mechanical properties of the composite while an outer layer can be selected to enhance or to provide the ability to utilize existing manufacturing technology. For example, outer layers of pyrolytic carbon can be machined and polished efficiently using existing polishing equipment and polishing media.

Also, outer layers of the composite can be selected to provide a better finish, such as an increased density for less pitting. Higher density, less porous material can be formed by reducing the coating rate by reducing the reactant feed rate, the temperature, or the bed weight in the reactor. The bed weight is the aggregate weight of the fluidized bed beads and substrates. In addition, inner layers of the composite can be selected to be advantageous for the removal of the substrate. For example, an inner layer, such as pyrolytic carbon, may provide processing advantages for the removal of the substrate.

Carbide layers provide desirable mechanical properties to the composites, as described further below. Gradient layers ensure that there are no abrupt changes in composition at interfaces so that the composite is stable with respect to delamination and wear.

Various forms of carbon are known, either in pure elemental carbon form or as doped solid carbon. The crystalline forms of elemental carbon include diamond with $sp^3$ bonding and graphite with $sp^2$ bonding. Graphite is anisotropic with strong in plane bonding and weak bonding between planes. Amorphous carbon is also known with varying degrees of $sp^2$ and $sp^3$ bonding. Carbon that is generally amorphous can have graphitic domains.

Pyrolytic carbon is formed from the decomposition or pyrolysis of carbon-containing compounds, such as volatile hydrocarbons. Thick coatings of pyrolytic carbon and pyrolytic graphite are formed by chemical vapor deposition (CVD) or by variants of CVD, such as plasma-enhanced CVD or plasma-assisted CVD. Pyrolytic graphite is generally formed at higher temperatures than those used to form pyrolytic carbon.

Pyrolytic graphite is an anisotropic material in which planar layers of graphitic carbon extend for considerable distances, resulting in an apparent crystallite size on the order of about 100 nm. Pyrolytic carbon is an isotropic material with a relatively disordered turbostratic graphitic structure, without excessive planar layers. Apparent crystallite sizes for pyrolytic carbon are typically on the order of about 3 nm to about 5 nm. The apparent crystallite size is determined from the width of specific peaks in the X-ray diffraction spectrum of the material.

Since pyrolytic carbon is composed of minute crystallites with essentially random orientation, its mechanical properties, such as hardness and strength, are essentially isotropic, i.e., uniform in all directions. In contrast, pyrolytic graphite is composed of relatively large, oriented crystallites and, therefore, its mechanical properties are anisotropic, i.e., not uniform in all directions. For example, pyrolytic graphite is stronger in directions parallel to the graphitic planes than in directions perpendicular to the planes. For forming the pyrolytic carbon-carbide composites, pyrolytic carbon, i.e., isotropic carbon, is preferred over pyrolytic graphite, since anisotropic graphitic carbon can delaminate due to its weak interplane forces.

The volume percent of pyrolytic carbon and the metal/metalloid carbide present in the composite material can be determined through chemical analysis. Suitable analytical methods include, for example, X-ray fluorescence (XRF), scanning electron microscope methods, such as wavelength dispersive and energy dispersive X-ray analysis (EDXA), Auger electron spectroscopy (AES), and X-ray photoelectron spectroscopy (XPS). Each of these analytical methods can quantify the elemental composition of a location very near or at the surface of a material. Preferred approaches include AES and XPS, also called electron spectroscopy for chemical analysis (ESCA). AES and XPS are also capable of providing information on the chemical binding of the elements in the material.

The volume percent compositions of the interior of a composite material can be determined using XPS and AES. First, a sample of the material is sectioned normal to the plane of the coating layers. A region of the cross section is analyzed by XPS or AES in scanning mode. The atomic percent concentrations of the elements present are determined. Since the metal/metalloid carbide chemical composition is known or can be determined by standard procedures from XPS and/or X-ray diffraction methods, the area percent attributable to the metal/metalloid carbide is thereby determined. Since the coating process generally produces layers, including transition layers, of relatively uniform thickness, the volume percent is readily estimated. To obtain even more accurate readings, successive parallel sections can be obtained for surface analysis by terminating the deposition at the layer of interest or by mechanical grinding or sectioning of the composite. For the purposes of identifying compositions within a gradient layer with varying composition across a measurable distance, the composition can be defined within a thin measurement layer such that a useful measurement can be made of the composition.

During the deposition of the pyrolytic carbon, additional components can be codeposited with the pyrolytic carbon to form an alloy or doped carbon with correspondingly modified properties. Pyrolytic carbon referred to herein has greater than about 50 percent by volume pyrolytic carbon, preferably at least about 75 percent by volume pyrolytic carbon, more preferably at least about 80 percent by volume pyrolytic carbon, and even more preferably at least about 90 percent by volume pyrolytic carbon.

Small amounts of a carbide composition can be alloyed with the pyrolytic carbon to increase the strength and/or wear resistance of the pyrolytic carbon. It is believed that up to about 20 volume percent carbide can be codeposited with the pyrolytic carbon without detracting from the thromboresistant character of the pyrolytic carbon. Suitable carbides for alloying with the pyrolytic carbon include, for example, silicon carbide (SiC), boron carbide ($B_4C$), tungsten carbide (WC, $W_2C$), tantalum carbide (TaC, $Ta_2C$), niobium carbide (NbC, $Nb_2C$), vanadium carbide (VC, $V_2C$), molybdenum carbide (MoC, $Mo_2C$), aluminum carbide ($Al_4C_3$), zirconium carbide (ZrC), titanium carbide (TiC), hafnium carbide (HfC) and mixtures thereof. Generally, the pyrolytic carbon-carbide alloy is deposited as a mixture where the metal/metalloid carbide and the pyrolytic carbon reside in distinct domains or phases.

The inclusion of metal/metalloid boride, metal/metalloid nitride and/or boron nitride is also contemplated. Boron or boride can be introduced into the coating by including a boron-containing gas, such as an alkyl boron, e.g., trimethylboron, a boron halide and/or a boron hydride, in the reactant gases flowing into the reactor. A nitride can be introduced into the coating by including a nitrogen containing gas, such as ammonia vapor, in the reactant gases flowing into the reactor. These reactions can take place over similar temperature ranges as the carbide reactions. The introduction of nitrides into coatings is described further in U.S. Pat. No. 4,505,720 to Gabor et al. and U.S. Pat. No. 4,900,526 to Matsuda et al., both of which are incorporated herein by reference.

Carbide layers, as described above, include greater than about 50 volume percent metal/metalloid carbide. The carbide layers can be essentially pure carbides. Preferably, the carbide layers are at least about 75 volume percent carbide, more preferably at least about 85 volume percent carbide and even more preferably at least about 90 volume percent carbide. Suitable carbide compounds include, for example, silicon carbide (SiC), boron carbide ($B_4C$), tungsten carbide (WC, $W_2C$), tantalum carbide (TaC, $Ta_2C$), niobium carbide (NbC, $Nb_2C$), vanadium carbide (VC, $V_2C$), molybdenum carbide (MoC, $Mo_2C$), aluminum carbide ($Al_4C_3$), zirconium carbide (ZrC), titanium carbide (TiC), hafnium carbide (HfC) and mixtures thereof. Silicon carbide is an especially preferred carbide.

The carbide compositions can include minority amounts of pyrolytic carbon, for example, at least about 1 percent by volume pyrolytic carbon. Similarly, the carbide compositions can include minority amounts of metal/metalloid nitrides or borides. The carbide compositions can include at least about one percent by volume and generally include less than about 10 volume percent metal/metalloid nitride or borides, preferably less than about 8 volume percent metal/metalloid nitride or boride, and more preferably from about one volume percent to about 5 volume percent metal/metalloid nitride or boride.

Reference to a pyrolytic carbon layer or a carbide layer refers to a layer with an effectively constant composition without reference to possible microdomains within the materials. As noted above, embodiments of the composites also can include at least one gradient layer with an effectively continuously varying composition within the gradient layer. The composition can, but does not necessarily, vary monotonically through the gradient layer. When used as a transition layer between a pyrolytic carbon layer and a carbide layer, a gradient layer generally includes at least one location in the gradient layer along the gradient at which the composition corresponds to a pyrolytic carbon compound as described above and at least one location at which the composition corresponds to a carbide compound, as described above.

In some embodiments, a gradient layer includes at least one region along the gradient with a majority composition of pyrolytic carbon and at least one other region with a majority composition of carbide. In particular, in some preferred embodiments, a gradient layer is located between a pyrolytic carbon layer and a carbide layer. In these embodiments, the gradient layer may be oriented such that the interface layer of the gradient layer at the interface with the pyrolytic carbon layer may have a composition identical or similar to the composition of the pyrolytic carbon layer. Similarly, the interface layer of the gradient layer at the carbide interface may have a composition identical or similar to the composition of the carbide layer.

In other preferred embodiments, the composite material includes only a gradient layer. For example, the two outer surfaces of the gradient material can have compositions of a pyrolytic carbon material. The outer surfaces generally would contact the patient's fluids and/or tissues. An inner portion of the gradient material may have a composition of a carbide material, although the composition of the carbide is continuously varying. See FIGS. 7 and 8 above, wherein the optional substrate can be removed.

As noted above, a substrate material is used to form the device component, although the substrate can be removed following deposition of the composite such that the substrate is optional in the finished composite in the embodiments shown in FIGS. 4-9. Suitable substrate materials include refractory metals, silicon carbide, ceramics, such as mullite ($Al_6Si_2O_{13}$) or zirconia (ZrO), and graphites. Suitable refractory metals include, for example, cobalt, tungsten, tantalum, niobium, vanadium, molybdenum, zirconium, titanium and alloys and mixtures thereof. To form well-bonded composite layers, a metal carbide layer can be deposited adjacent to a metal substrate, where the metal carbide preferably is based on the same metal or one of the same metals of the substrate, in the case of an alloy. Thus, a strong bond can be formed between the metal substrate and the adjacent metal carbide coating. Similarly, if a graphite substrate is used, a pyrolytic carbon coating can be placed adjacent to the substrate to form a strong bond between the graphite substrate and the pyrolytic carbon coating. If the substrate is to be subsequently removed, the coating over the substrate can be selected to form a particularly weak bond, as described further below.

In preferred embodiments, throughout the composite there are no interfaces, including interfaces with substrates that are to be included in the composite, with abrupt changes in the coefficient of thermal expansion. Abrupt changes in the coefficient of thermal expansion can lead to cracking and delamination due to changes in temperature during the coating process or during cooling from the chemical vapor deposition reaction temperature. However, abrupt changes are found with certain substrates, such as refractory metals, and may be satisfactory with respect to thermal stability. Similarly, abrupt changes in crystal structure at interfaces within the composite are preferably reduced or eliminated to reduce correspondingly the risk of cracking and/or delamination.

The thickness of the composite material generally ranges from about 0.1 mm to about 5 mm, preferably from about 0.2 mm to about 3 mm, and more preferably from about 0.2 mm to about 1.5 mm. For many applications, thinner components are preferred. For example, a thinner heart valve orifice ring provides a larger orifice lumen for blood flow. Similarly, thinner heart valve occluders/leaflets generally have better hemodynamic characteristics and open and close more responsively during the cardiac cycle.

Nevertheless, the material must be thick enough to have satisfactory mechanical performance relating to fracture resistance and durability. In particular, the medical device can be subject to fracture due to forces inadvertently applied to the device during implantation. Similarly, the material is subject to wear and potentially to fatigue over an extended period of use.

The carbide material contributes to an increase in fracture resistance and strength for device components that are thin. As a result, composites, especially those without substrates, can be thinner without sacrificing desirable levels of mechanical performance. Furthermore, the use of stiffening or reinforcing metal rings for substrateless pyrolytic carbon orifices, as found on commercially available mechanical heart valves, can be avoided. Avoiding the use of reinforcing rings allows for more efficient use of the tissue annulus that remains after the patient's native valve is excised.

The composites can be produced with substantially uniform thickness throughout the composites. Alternatively, the thickness can be varied at different portions of the material. Variations in the thickness can be used to shape the component for desirable performance characteristics, such as flow over the surfaces of the components. For example, an occluder for a bileaflet heart valve prosthesis preferably has a desirable shape for approximately laminar flow past the leaflet and for responsive opening and closing in response to the cardiac cycle flow. Leaflets with a downstream profile thinner than an upstream profile can be formed, and vice versa. Similarly, the orifice ring, and especially its lumen, can be provided with a desirable hemodynamic shape. In addition, the shape of the material can be varied to achieve desirable mechanical performance without unnecessarily increasing the total mass of the component. For example, the material can be made thicker at stress points to reduce the risk of structural failure.

A composite with a non-uniform thickness can be formed using a shaped substrate with a non-uniform thickness. If the coatings are applied approximately uniformly over the shaped substrate, the resulting composite material has a thickness that reflects the nonuniform thickness of the underlying substrate, although the coating process tends to smooth edges and the like. Alternatively, variations in thickness can be produced by changing the coating thickness at different locations on the substrate, whether or not the substrate is ultimately removed. The coating thickness can be varied by depositing the coating with different thicknesses at various locations or by machining away the coating at select locations. A combination of substrate shape and coating thickness variation can be used to achieve a desired shape and thickness variation of the final material. Also, the shape of the composite article can be produced as a negative image of a substrate surface, the substrate then being removed, for example, by abrasive machining.

Additionally, with some deposition approaches, such as static bed vapor deposition and plasma-assisted chemical vapor deposition, the composition of the composite can be varied at different locations of the composite material. Variation in the composition can be used, for example, to provide added structural strength at stress points. In particular, additional carbide thickness relative to pyrolytic carbon thickness or a higher percent carbide can be deposited at anticipated stress points in the material.

Deposition Approaches

Generally, pyrolytic carbon is deposited by the pyrolysis of a hydrocarbon gas, typically in a temperature range from about 1000° C. to about 2500° C. With propane as the hydrocarbon source, the preferred temperature range is from about 1100° C. to about 1800° C. The temperature range can be varied according to precursors used. At least some carbides can be conveniently deposited by comparable pyrolysis. Thus, introduction of the appropriate blend of precursor compounds into the pyrolytic reactor results in the production of the appropriate material, either pyrolytic carbon, carbide compound or mixtures thereof.

If the precursors of the pyrolytic carbon and the metal/metalloid carbide are blended in the reaction vapor, an alloy of the pyrolytic carbon and carbide materials is formed where the two materials are mixed in the sense that grains or crystallites of each material form domains or phases adjacent to domains or phases of the other material. The deposition methods include, without limitation, chemical vapor deposition, plasma assisted chemical vapor deposition and fluidized bed chemical vapor deposition. In particular, chemical vapor deposition can be performed in a fluidized reactor. Liquid phase chemical vapor deposition is also possible. Liquid phase vapor deposition is described generally in "Liquid fluidized bed coating process," by Lackey in the journal Carbon 34(10):1299-1300 (1996). Fluidized bed chemical vapor deposition is a preferred method. The temperature and/or other reactor variables, such as vapor flow rates, can be varied during the deposition of the composite depending on the composition being deposited at a particular point in time.

Suitable pyrolytic carbon precursors include, for example, hydrocarbon gases, such as methane, ethane, propane, ethylene, acetylene, and mixtures thereof. Suitable silicon carbide pyrolysis precursors include, for example, methyl silane ($CH_3SiH_3$), and methyl trichlorosilane ($CH_3SiCl_3$). Metal carbide precursors can include metal halogens, such as metal chlorides, in which the metal is the desired metal for the corresponding metal carbide. The hydrocarbon gas or an inert gas, such as argon, nitrogen, helium, or mixtures thereof, can be bubbled through a liquid carbide precursor to serve as a carrier gas that assists with the delivery of desired amounts of the vapor of the precursor compound. A nitrogen containing compound can be included for the deposition of a quantity of metal/metalloid nitride.

In one approach to the pyrolysis reaction, the reactant vapors are directed into a reaction furnace. The substrate is mounted in the reaction furnace. The furnace generally is kept at a wall temperature from about 1000° C. to about 2500° C. using any reasonable heating approach, such as induction, radiant or resistance heating. Generally, higher temperatures are used for the deposition of the carbides than for the deposition of pyrolytic carbon. The particular preferred temperature will depend on the particular precursors, flow rate and reactor design. With some deposition approaches, the substrate can be rotated to obtain an even coating. Similarly, the substrate can be movable to provide desired variation in the coating thickness at different locations on the substrate depending on the orientation of the substrate with respect to reaction flow over the course of the entire coating process.

In a preferred approach, the pyrolysis reaction/chemical vapor deposition is performed in a fluidized bed reactor. In particular, the substrate is placed within a bed of particles, such as zirconia beads, that are fluidized by the flow of reactant and carrier gases. Pyrolytic carbon can be deposited within a fluidized bed reactor using hydrocarbon gases as reactants. The fluidized bed reactor preferably is set at a temperature selected in part upon the particular reactant gases and is typically at a temperature from about 1000° C. to about 2500° C. and more preferably from about 1100° C. to about 1800° C. Alternatively, the reaction can be performed in a liquid-phase chemical vapor deposition reactor. In this liquid-phase process, the reagents are liquids that are fluidized by the flow of inert gases. A liquid fluidized bed deposition process is described further in Lackey et al., "Liquid Fluidized Bed Coating Process," Carbon 34 (10):1299-1300 (1996).

Referring to FIG. 13, a fluidized bed reactor is displayed. The fluidized bed reactor 400 includes a reaction chamber 402 within a furnace 404. Component preforms (substrates) 406 to be coated are placed within reaction chamber 402 along with beads 408. Reactant and carrier gases are flowed through reaction chamber 402 from neck 410, according to the flow arrow of FIG. 13. The gas flow fluidizes or levitates beads 408 and components 406. Components of a heart valve prosthesis, including an orifice ring 412 and a leaflet 414, after coating is shown in an expanded cross sectional view.

For substrateless embodiments, the substrate can be removed by abrading or grinding the substrate, after exposing the substrate by mechanical removal of any overlying coating. Removal of the substrate can be aided by forming a weak interface between the substrate and a coating adjacent the substrate that is readily fractured or abraded. For example, a soft pyrolytic carbon can be used as the coating immediately adjacent to a graphite substrate such that the graphite-pyrolytic carbon interface can be machined away. Similarly, appropriate substrates can be abraded away. In particular, graphite is a soft material that can be machined or ground with an abrasive. The grinding can be performed to not significantly remove any of the coating materials desired for the final component.

Properties of Metal/Metalloid Carbide—Pyrolytic Carbon Composites

The composite materials can incorporate desirable features from each of the component materials. The composite then is an excellent material for the formation of rigid medical devices and/or rigid components of medical devices. For example, pyrolytic carbon has desirable surface characteristics for contacting blood flow including, for example, a desirable thromboresistant characteristic. Thus, the composite preferably has a pyrolytic carbon surface layer on exposed surfaces intended to contact blood flow.

The metal/metalloid carbide materials have a high mechanical strength and resistance to fracture. Carbide compositions have a greater mechanical strength than many materials suitable for use as the substrate, although carbides themselves can be used as the substrate. In addition, the carbides are very stiff. Thus, the composite materials can be very strong and very stiff, which makes them suitable for rigid medical devices or components thereof.

The composite material generally has a stiffness corresponding to a Young's modulus greater than about 5 million psi, and preferably greater than about 7 million psi. Thus, thinner materials can be used without sacrificing desired stiffness for rigid components. In addition, the composite generally has a fracture toughness greater than about $2 \text{ MPa(m)}^{0.5}$, and preferably greater than about $3 \text{ MPa(m)}^{0.5}$. Due to the increased fracture resistance, it is less likely that a prosthetic device made from the composites will be damaged during implantation by accidently exerting force against the component, such as with a metal tool, for example, a hemostat or forceps, in comparison with an equivalent device produced from conventional pyrolytic carbon materials.

Completion of the Medical Device, Storage, Packaging, Distribution and Use

The pyrolytic carbon/carbide composite material can form an entire medical device, or the composite can be incorporated with other biocompatible components into a medical device. For example, a pyrolytic carbon/carbide composite forming an orifice ring can be incorporated into a heart valve prosthesis, prior to storage and/or distribution of the resulting prosthesis. The orifice ring can be combined with one or more occluders and a sewing ring to complete the prosthesis.

The pyrolytic carbon/carbide composite can be stored appropriately prior to or following formation into a medical device. Generally, the composite material would be stored in a dry, sterile environment. If components of the medical device require moisture to maintain their integrity, such as tissue or hydrogel components, the medical device with the pyrolytic carbon/carbide composite can be stored in a moist, sterile environment. The moist environment can be maintained with or without immersing the medical device in a sterile liquid, such as aqueous glutaraldehyde.

For distribution, the medical devices are placed in sealed and sterile containers. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis and the like.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A heart valve prosthesis comprising a graphite substrate having a coating over at least a portion of its surface, the coating comprising a first layer adjacent the substrate at least about 50 percent by volume pyrolytic carbon and less than about 50 percent by volume carbide composition, a second layer adjacent the first layer comprising at least about 50 volume percent carbide composition, a third layer adjacent the second layer comprising at least about 50 volume percent pyrolytic carbon and no more than about 50 volume percent carbide composition, and a surface layer adjacent the third layer comprising at least about 80 volume percent pyrolytic carbon.

2. The heart valve prosthesis of claim 1 wherein the surface of the substrate comprises two opposite surfaces, at least a portion of each surface being covered with a coating.

* * * * *